United States Patent
Hong et al.

(10) Patent No.: US 9,399,690 B2
(45) Date of Patent: Jul. 26, 2016

(54) SILICA SUPPORT, PREPARATION METHOD THEREOF AND METALLOCENE CATALYST USING THE SAME

(71) Applicant: LG CHEM, LTD., Seoul (KR)

(72) Inventors: Dae Sik Hong, Daejeon (KR); Ki Soo Lee, Daejeon (KR); Heon Yong Kwon, Daejeon (KR); Hyeon-Gook Kim, Daejeon (KR); Eun Kyoung Song, Daejeon (KR); Yong Ho Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/426,656

(22) PCT Filed: Feb. 5, 2014

(86) PCT No.: PCT/KR2014/000984
§ 371 (c)(1),
(2) Date: Mar. 6, 2015

(87) PCT Pub. No.: WO2014/204079
PCT Pub. Date: Dec. 24, 2014

(65) Prior Publication Data
US 2015/0240010 A1    Aug. 27, 2015

(30) Foreign Application Priority Data

Jun. 18, 2013 (KR) .................. 10-2013-0069902
Feb. 4, 2014 (KR) .................. 10-2014-0012669

(51) Int. Cl.

| | |
|---|---|
| C08F 4/02 | (2006.01) |
| C08F 4/6592 | (2006.01) |
| C08F 10/00 | (2006.01) |
| C08F 210/02 | (2006.01) |
| C08F 4/659 | (2006.01) |
| C07F 7/08 | (2006.01) |
| C08F 10/02 | (2006.01) |
| B01J 21/08 | (2006.01) |
| B01J 31/06 | (2006.01) |
| B01J 31/14 | (2006.01) |
| B01J 31/16 | (2006.01) |
| B01J 31/22 | (2006.01) |
| C08F 110/02 | (2006.01) |

(52) U.S. Cl.
CPC ............... *C08F 210/02* (2013.01); *C07F 7/087* (2013.01); *C07F 7/0876* (2013.01); *C08F 4/02* (2013.01); *C08F 4/65916* (2013.01); *C08F 10/02* (2013.01); *B01J 21/08* (2013.01); *B01J 31/069* (2013.01); *B01J 31/143* (2013.01); *B01J 31/1616* (2013.01); *B01J 31/2295* (2013.01); *B01J 2531/48* (2013.01); *C08F 4/65912* (2013.01); *C08F 4/65925* (2013.01); *C08F 110/02* (2013.01); *Y02P 20/52* (2015.11)

(58) Field of Classification Search
CPC .... C08F 4/02; C08F 4/65008; C08F 4/65912; C08F 4/65916; C08F 10/00
See application file for complete search history.

(56) References Cited

U.S. PATENT DOCUMENTS

| | | | | |
|---|---|---|---|---|
| 5,346,872 | A | * 9/1994 | Menon | ................. B01J 31/0212 502/113 |
| 5,424,263 | A | 6/1995 | Buehler | |
| 5,583,085 | A | * 12/1996 | Ward | ....................... B01J 21/08 502/176 |
| 5,616,665 | A | 4/1997 | Jejelowo et al. | |
| 5,925,587 | A | 7/1999 | Lee et al. | |
| 6,469,113 | B1 | * 10/2002 | Lee | ......................... C07F 17/00 502/120 |

FOREIGN PATENT DOCUMENTS

| | | | |
|---|---|---|---|
| CN | 1263537 | A | 8/2000 |
| CN | 100362024 | C | 1/2008 |
| CN | 101412767 | A | 4/2009 |
| CN | 101633703 | A | 1/2010 |
| CN | 101906179 | A | 12/2010 |
| JP | H05194640 | A | 8/1993 |
| JP | H09164512 | A | 6/1997 |
| KR | 10-1996-0007624 | A | 3/1996 |
| KR | 10-0178954 | B1 | 11/1998 |
| KR | 10-1999-0036831 | A | 5/1999 |
| KR | 10-2004-0085650 | A | 10/2004 |
| KR | 10-0579843 | B1 | 5/2006 |
| KR | 10-2011-0101386 | A | 9/2011 |
| KR | 10-1203772 | B1 | 11/2012 |
| KR | 10-2013-0027316 | A | 3/2013 |
| WO | 2011/111980 | A2 | 9/2011 |

* cited by examiner

*Primary Examiner* — Caixia Lu
(74) *Attorney, Agent, or Firm* — Dentons US LLP

(57) ABSTRACT

This disclosure relates to a silica support for a metallocene catalyst used for olefin polymerization, a preparation method thereof, a metallocene catalyst using the same, and olefin polymer. Specifically, according to the present invention, a silica support used for preparing a metallocene supported catalyst is treated with a specific halogenized metal compound, thereby diversifying reaction sites to a cocatalyst when preparing a metallocene catalyst, and thus, the molecular weight distribution of produced olefin polymer may be much broadened and polymer having high molecular weight may be obtained compared to the existing support, even if the same metallocene catalyst is supported.

9 Claims, No Drawings

SILICA SUPPORT, PREPARATION METHOD THEREOF AND METALLOCENE CATALYST USING THE SAME

This application is a National Stage Entry of International Application No. PCT/KR2014/000984, filed on Feb. 5, 2014, which claims priority to and the benefit of Korean Patent Application No. 10-2013-0069902, filed on Jun. 18, 2013 and Korean Patent Application No. 10-2014-0012669 filed on Feb. 4, 2014, both of which are incorporated herein by reference in their entirety.

TECHNICAL FIELD

The present invention relates to a silica support for a metallocene catalyst used for olefin polymerization, which may diversify reaction sites, a preparation method thereof, a metallocene catalyst using the same, and olefin polymer.

BACKGROUND

Since a Ziegler-Natta catalyst widely applied for the existing commercial process is a multisite catalyst, the molecular weight distribution of the produce polymer is broad, and the chemical composition distribution of the comonomers is not uniform, and thus, there is a limit in achieving desired properties.

To the contrary, a general metallocene catalyst is a single site catalyst having one kind of active site, and the polymer produced using the same has narrow molecular weight distribution, and the molecular weight, stereoregularity, crystallinity, and particularly, reactivity of comonomers may be substantially controlled according to the structures of the catalyst and ligand.

The metallocene catalyst system consists of a main catalyst including a transition metal compound, particularly a Group 4 metal of the Periodic Table as a main component, and an organometallic compound cocatalyst including Group 13 metal such as aluminum as a main component. As the catalyst has single site, polymer such as polyolefin having narrow molecular weight distribution may be prepared using the same.

The molecular weight and the molecular weight distribution of polyolefin are important factors for determining physical properties, flow influencing on the processability, and mechanical properties of the polymer. To prepare various polyolefin products, it is important to improve melt processability through the control of molecular weight distribution. Particularly, in the case of polyethylene, toughness, strength, environmental stress resistance and the like are very important. Thus, a method of improving the mechanical properties of high molecular weight resin and the processability of low molecular weight resin by preparing polyolefin having bimodal or wide molecular weight distribution is suggested.

Meanwhile, as a support for a supported catalyst, silica is generally used, and a cocatalyst methylaluminoxane (MAO) and at least one organometallic catalyst (for example, a metallocene catalyst) are supported on the support to prepare a supported catalyst.

However, this method has a limitation in broadening molecular weight distribution because only one active site exists, and the utilization of siloxane groups on the surface is lowered, and thus, when polyolefin is prepared using the same, catalytic activity is low and olefin polymer having high molecular weight cannot be prepared.

Accordingly, there is a demand for the development of a novel catalyst that has improved catalytic activity and can prepare polyolefin having wide molecular weight distribution.

DISCLOSURE

Technical Problem

It is an object of the present invention to provide a silica support for a metallocene catalyst that may improve selectivity to olefin polymer and catalytic activity, and may diversify reaction sites to a cocatalyst so that the molecular weight distribution of the produced polyolefin may be broadened and the polyolefin may have high molecular weight, and a method for preparing the same.

It is another object of the present invention to provide a metallocene catalyst prepared using the silica support, and olefin polymer obtained using the same.

Technical Solution

The present invention provides a silica support having at least reaction sites of —OH; —O-alkaline earth metal-halogen or —O-alkylene-alkaline earth metal-halogen; and —O-alkyl; on the silica surface.

The present invention also provides a method for preparing the silica support comprising
(a) heat treating a silica-based support; and
(b) treating the heat treated silica with 0.05 to 2 mmol/g-silica of an alkoxyalkyl-alkyline earth metal-halogen compound.

The present invention also provides a metallocene catalyst comprising the above explained silica support; a metallocene compound; and a cocatalyst.

The present invention also provides olefin polymer obtained by copolymerizing at least one olefin monomer in the presence of the above explained metallocene catalyst.

Advantageous Effects

According to the present invention, catalytic activity may be increased by using a specific silica support having diversified reaction sites compared to the existing one when preparing a supported metallocene catalyst. Thus, olefin polymer having higher molecular weight and broadened molecular weight distribution may be prepared.

BEST MODE

Hereinafter, a method for preparing a supported metallocene catalyst and a hybrid supported metallocene catalyst and the like according to the present invention will be explained in detail.

According to one embodiment of the invention, provided is a silica support having at least reaction sites of —OH; —O-alkaline earth metal-halogen or —O-alkylene-alkaline earth metal-halogen; and —O-alkyl; on the silica surface.

Although silica used for preparing a supported metallocene catalyst is just heat treated, it is difficult to increase catalytic activity and broaden molecular weight distribution because only one reaction active site exists when supporting a cocatalyst and a metallocene catalyst.

However, since the silica support of the present invention includes at least the above 3 kinds of reaction sites on the surface, it may increase reaction active sites to a cocatalyst and a metallocene compound that are used when preparing a supported metallocene catalyst to at least 3. Thus, according to the present invention, when preparing olefin polymer, molecular weight distribution may be broadened, and a supported metallocene catalyst having high molecular weight may be provided. And, due to the use of the silica support, the activity of the supported metallocene catalyst may be increased to prepare polyolefin having high molecular weight with high yield.

The reaction site refers to a site that can react with a metallocene compound, a cocatalyst or a mixture thereof so that the metallocene compound and cocatalyst may be supported.

More preferably, in the present invention, as shown in the Reaction Formula 1, hydroxyl groups existing on the surface of a silica support is heat treated, and then, treated with $R_1OR_2MgCl$ (wherein, $R_1$ is a C1-10 alkyl group, $R_2$ is a C1-10 alkylene group)(3), thereby preparing a silica support such as a compound of the Chemical Formula 2. And then, a cocatalyst (MAO) and a metallocene compound (Cat) are supported thereon to prepare a supported metallocene catalyst of the Chemical Formula 1.

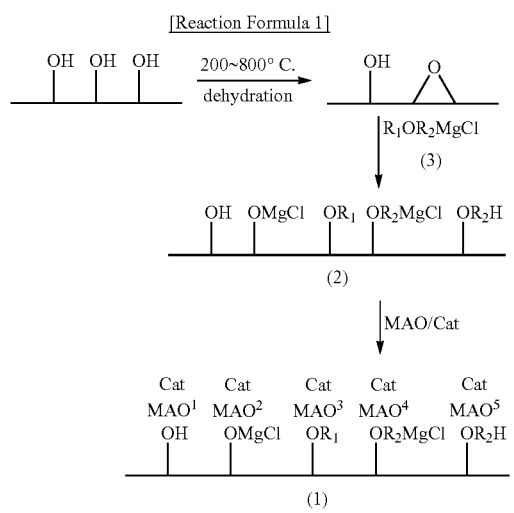

(wherein, $R_1$ is a C1-10 alkyl group, $R_2$ is a C1-10 alkylene group)

The silica support of the Chemical Formula 2 of the present invention includes 4 reaction sites as explained above, and the —O-alkyl may include —$OR_1$, —$OR_2H$.

Therefore, the silica support of the Chemical Formula 2 of the present invention includes reaction sites of —OH, —O—MgCl, —$OR_1$, —$OR_2MgCl$ and —$OR_2H$. Thus, a cocatalyst MAO and a metallocene compound are supported on each of the 5 or more reaction sites to provide a supported metallocene catalyst of the Chemical Formula 1.

Thus, it is preferable that the silica support of the present invention may include reaction sites of —OH, —O—MgCl, —$OR_1$, —$OR_2MgCl$ and —$OR_2H$ (wherein, $R_1$ is a C1-10 alkyl group, and $R_2$ is a C1-10 alkylene group) on the surface.

The silica support may preferably have BET surface area of 200 to 800 $m^2/g$ and average particle diameter of 5 to 100 μm.

And, the silica may further include oxide, carbonate, sulfate or nitrate of $Na_2O$, $K_2CO_3$, $BaSO_4$, or $Mg(NO_3)_2$. Wherein, the silica may refer to a silica before or after heat treatment.

Meanwhile, according to another embodiment of the invention, provided is a method for preparing the above explained silica support comprising (a) heat treating a silica-based support; and (b) treating the heat treated silica with 0.05 to 2 mmol/g-silica of an alkoxyalkyl-alkaline earth metal-halogen compound.

In the step (a), the silica-based support may be preferably heat treated at a temperature of 200 to 800° C. for 1 to 48 hours. If the drying temperature of the support is less than 200° C., excess moisture may exist and thus the moisture on the surface may react with a cocatalyst, and if the temperature is greater than 800° C., the pores on the surface of the support may be combined to decrease surface area, and a lot of hydroxyl groups may disappear on the surface and only siloxane groups may remain, thus decreasing the reaction sites with a cocatalyst, which is not preferable.

As the silica-based support, silica, silica-alumina or silica-magnesia may be preferably used. And, the support in the step (a) may comprise hydroxyl groups on the surface. And, the silica-based support may further comprise oxide, carbonate, sulfate or nitrate of $Na_2O$, $K_2CO_3$, $BaSO_4$, or $Mg(NO_3)_2$.

The amount of the hydroxyl groups may be controlled by the support preparation method and conditions or drying conditions (temperature, time, drying method and the like). For example, it is preferable that the amount of the hydroxyl groups on the surface of the support becomes 0.1~10 mmol/g, and more preferably 0.5~3 mmol/g. If the amount of the hydroxyl group is less than 0.1 mmol/g, reaction sites with a cocatalyst may decrease, and if it is greater than 10 mmol/g, it is possible that the hydroxy groups may be derived from the moisture other than the hydroxy groups existing on the surface of the support, which is not preferable.

At this time, in order to reduce side reactions by a small amount of hydroxyl groups remaining after drying, a support from which hydroxyl groups are chemically removed while conserving siloxane groups that participate in supporting and have high reactivity may be used.

In this case, the support preferably has highly reactive hydroxyl groups and siloxane groups together on the surface. Specific examples of the support may include silica, silica-alumina, or silica-magnesia and the like, which are dried at high temperature, and it may commonly further include oxide, carbonate, sulfate or nitrate of $Na_2O$, $K_2CO_3$, $BaSO_4$, or $Mg(NO_3)_2$ and the like.

And, it is preferable that the step (b) may further comprise a step of progressing the reaction of the silica heat treated at 0 to 100° C. and an alkoxyalkyl-alkaline earth metal-halogen compound. By mixing the heat treated silica and the alkoxy-alkyl-alkaline earth metal-halogen compound through the step (b), a slurry may be formed.

And, the amount of the alkoxyalkyl-alkaline earth metal-halogen compound that is used to surface treat the silica-based support is also important, and it is preferably 0.05 to 2 mmol/g-silica, based on the weight of the silica-based support.

And, the alkoxyalkyl-alkaline earth metal-halogen compound may include an alkoxy group and a halogen compound, and for example, a compound represented by the following Chemical Formula 3 may be used.

$R_1OR_2MX$ [Chemical Formula 3]

(wherein, $R_1$ is a C1-10 alkyl group, $R_2$ is a C1-10 alkylene group, M is an alkaline earth metal, and X is a halogen atom)

In the compound of the Chemical Formula 3, it is preferable that M is Mg, and X is Cl. And, specific examples of the Chemical Formula 3 includes t-BuO(CH$_2$)$_6$MgCl.

Meanwhile, according to yet another embodiment of the invention, provided is a metallocene catalyst comprising the above explained silica support having diversified reaction sites; a metallocene compound; and a cocatalyst.

The metallocene compound may be represented by the following Chemical Formula 4.

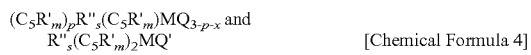  [Chemical Formula 4]

(wherein,

M's are independently a transition metal of Group 4, 5 or 6 of the Periodic Table; at least one $C_5R'_m$ is substituted cyclopentadienyl;

R's, which may be identical or different, are independently hydrogen, a C1-20 alkyl, a C2-20 alkenyl, a C6-20 aryl, a C7-20 alkylaryl or a C7-20 arylakyl radical (they may be linked to form a substituted or unsubstituted ring having 4 to 20 carbon atoms, or a part of the ring);

R", which crosslinks two $(C_5R'_m)$ rings or crosslinks one $(C_5R'_m)$ ring to M, is a radical containing carbon, germanium, silicon, phosphorus or nitrogen, or a combination thereof;

if p is 0, x is 1, otherwise "x" is always 0;

Q's, which may be identical or different, are independently a C1-20 alkyl, a C2-20 alkenyl, a C6-20 aryl, a C7-20 alkylaryl or a C7-20 arylakyl radical, halogen or alkoxide;

Q' is an alkylidene radical having 1 to 20 carbon atoms; s is 0 or 1, if s is 0, m is 5 and p is 0, 1 or 2, and if s is 1, m is 4 and p is 1)

Meanwhile, as the cocatalyst, those well known in the art may be used without specific limitations. For example, an organic aluminum-based compound may be used as the cocatalyst, and at least one selected from the group consisting of the compounds of the following Chemical Formula 5 and Chemical Formula 6 may be used.

  [Chemical Formula 5]

in the Chemical Formula 5, $R_3$, which are identical or different, are independently a halogen radical, a C1-20 hydrocarbyl radical, or a C1-20 hydrocarbyl radical substituted with halogen, and c is an integer of 2 or more,

  [Chemical Formula 6]

in the Chemical Formula 6, $R_4$ is a C1-20 hydrocarbyl or a C1-20 hydrocarbyl substituted with halogen.

The compound represented by the Chemical Formula 5 may include, for example, methylaluminoxane (MAO), ethylaluminoxane, isobutylalumninoxane, butylaluminoxane, and the like.

Among the compound represented by the Chemical Formula 5, alkylmetal compounds may include trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tollylaluminum, dimethylaluminummethoxide, dimethylaluminumethoxide, trimethylboron, triethylboron, triisobutylboron, tripropylboron, tributylboron and the like.

The compound of the Chemical Formula 6 may include triethylammoniumtetraphenylaluminum, tributylammoniumtetraphenylaluminum, trimethylammoniumtetraphenylaluminum, tripropylammoniumtetraphenylaluminum, trimethylammoniumtetra(p-tollyl)aluminum, tripropylammoniumtetra(p-tollyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrafluorophenylaluminum, diethylammoniumtetrapentafluorophenylaluminum, triphenylphosphoniumtetraphenylaluminum, trimethylphosphoniumtetraphenylaluminum, triphenylcarboniumtetraphenylaluminum and the like.

In addition, if necessary, the compounds represented by the following Chemical Formula 7 or 8 may be further used as a cocatalyst.

  [Chemical Formula 7]

  [Chemical Formula 8]

In the Chemical Formulae, L is neutral or cationic Lewis acid, H is a hydrogen atom, Z is boron, A is a C6-20 aryl or a C1-20 alkyl group wherein at least one hydrogen is substituted with halogen, a C1-20 hydrocarbyl group, an alkoxy group, a phenoxy group, nitrogen, phosphorus, sulfur or oxygen atom.

Specific examples of the compound of the Chemical Formula 7 or 8 may include trityltetrakis(pentafluorophenyl) borate, N,N-dimethylaniliniumtetrakis(pentafluorophenyl) borate, trimethylammonium tetrakis(pentafluorophenyl) borate, triethylammonium tetrakis(pentafluorophenyl)borate or tripropylammonium tetrakis(pentafluorophenyl)borate, but are not limited thereto.

And, the supported amount of the cocatalyst may be 0.1-20 mmol per 1 g of the silica support. If the supported amount of the cocatalyst is less than 0.1 mmol, the catalyst may not be activated, and if it is greater than 20 mmol, the cocatalyst may be released to cause fouling of the reactor.

When a cocatalyst and a metallocene compound are supported on the silica support of the present invention, it may be progressed appropriately using high temperature supporting and low temperature supporting. And, it may be progressed at a temperature of 25 to 100° C.

In the metallocene catalyst of the above explained one embodiment, the supported metallocene catalyst may comprise [aluminum metal of the cocatalyst]/[transition metal of the metallocene catalyst] at a mole ratio of 1~10,000, preferably 1~1,000, more preferably 10~100. If the mole ratio is less than 1, the content of aluminum metal of the primary cocatalyst may be too low, and thus, active catalytic species may not be sufficiently formed thus lowering the activity, and if the mole ratio is greater than 10,000, there is a concern that the aluminum metal may act as catalytic poison.

Meanwhile, according to another embodiment of the invention, provided is olefin polymer prepared by copolymerizing at least one kind of olefin monomers in the presence of the metallocene catalyst.

Specifically, the olefin polymer of the present invention may be prepared in the presence of a supported metallocene catalyst that is prepared using a silica support having at least 3 kinds of reaction sites of —OH; —O-alkaline earth metal-halogen; and alkoxy or —O-alkyl on the silica surface.

Thus, according to the present invention, production yield may be improved, and particularly, polyolefin (olefin polymer) having wide molecular weight distribution and high molecular weight may be prepared.

And, the supported metallocene catalyst of the present invention may be used by itself for olefin polymerization. And, selectively, the supported metallocene catalyst may be contacted with olefin monomers such as ethylene, propylene, 1-butene, 1-hexene, 1-octene and the like to prepare a prepolymerized catalyst.

The olefin monomer may include ethylene, propylene, alpha olefin, cyclic olefin and the like, and diene olefin monomers or triene olefin monomers and the like having two or more double bonds may be polymerized. More specifically, the olefin monomers may include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, norbornene, norbornadiene, ethylidene norbornene, phenyl norbornene, vinyl norbornene, dicylcopentadiene, 1,4-butadiene, 1,5-pentadiene, 1,6-hexadiene, styrene, alpha-methylstyrene, divinylbenzene and 3-chloromethylstyrene, and two or more kinds of these monomers may be mixed and copolymerized.

And, if the supported metallocene catalyst is used without prepolymerization, it may be diluted in an aliphatic hydrocarbon solvent having a carbon number of 5 to 12 such as isobutene, pentane, hexane, heptanes, nonane, decane, and isomers thereof, an aromatic hydrocarbon solvent such as toluene, benzene and the like, a hydrocarbon solvent substituted with a chlorine atom such as dichloromethane, chlorobenzene and the like, and injected. It is preferable that the solvent is treated with a small amount of aluminum so as to remove a small amount of water, air and the like, which may act as catalytic poison, prior to use.

And, the olefin polymer may be prepared in the form of a copolymer of ethylene and another comonomer. In this case, the comonomer may be at least one selected from the group consisting of propylene, 1-butene, 1-hexene and 4-methyl-1-pentene and 1-octene.

One kind of monomer may be homopolymerized or two or more kinds of monomers may be copolymerized using a continuous slurry polymerization reactor, a loop slurry reactor, a gas phase reactor, and the like.

The olefin polymer prepared by the above method may have weight average molecular weight of 50,000 to 400,000.

Hereinafter, the action and the effects of the invention will be explained in detail, with reference to specific examples. However, these examples are only to illustrate the invention, and the scope of the invention is not limited thereto.

As organic reagents and solvents required for the preparation of a catalyst and, polymerization, products from Aldrich Company were purified by a standard method prior to use, and as ethylene, high purity ethylene from Applied Gas Technology Inc., was passed through a moisture and oxygen filter prior to use. In all the steps of catalyst synthesis, support and olefin polymerization, contact with moisture and air was blocked to increase reproducibility of the experiment.

In order to prove the structure of a catalyst, spectrum was obtained using 300 MHz NMR (Bruker). The apparent density was measured according to DIN 53466 and ISO R 60 using an Apparent Density Tester 1132 (available from APT Institute fr Prftechnik).

Preparation Example 1

Preparation of Pretreated Silica Support

Silica (Grace Davison, SYLOPOL 948) was heat treated at a temperature of 600° C. for 12 hours under vacuum, to form siloxane groups on the surface. Thereafter, in a 300 ml reactor equipped with a stirrer, 10 g of the heat treated and dried silica and 5 mmol of t-BuO($CH_2$)$_6$MgCl were introduced so that the treated amount of t-BuO($CH_2$)$_6$MgCl may become 0.5 mmol/g-silica, and the mixture was stirred at 40° C. for 1 hour to progress the reaction and form a slurry.

Subsequently, the slurry was dried using a vacuum pump, thereby preparing a spherical silica support having an average particle diameter of 30 μm, the surface of which was treated with the t-BuO($CH_2$)$_6$MgCl.

Preparation Example 2

A silica support was prepared by the same method as Preparation Example 1, except changing the used amount of the t-BuO($CH_2$)$_6$MgCl so that the treated amount of t-BuO($CH_2$)$_6$MgCl may become 1.0 mmol/g-silica.

Preparation Example 3

A silica support was prepared by the same method as Preparation Example 1, except changing the used amount of the t-BuO($CH_2$)$_6$MgCl so that the treated amount of t-BuO($CH_2$)$_6$MgCl may become 1.5 mmol/g-silica.

Comparative Preparation Example 1

Silica (Grace Davison, SYLOPOL 948) was heat treated at a temperature of 600° C. for 12 hours under vacuum to prepare dried silica.

Example 1

Preparation of a Supported Metallocene Catalyst

In a 300 ml glass reactor where 100 μl of a toluene solution was placed, 5 g of the pretreated silica support of the Preparation Example 1 was introduced, followed by stirring while elevating the temperature of the reactor to 40° C.

And, a metallocene solution of a metallocene compound (nBuCp)$_2$ZrCl$_2$ 0.05 mmol/g-silica (silica refers to a complex support) and methylaluminoxane 30 ml (10 wt % solution, in toluene) was prepared so that the metallocene compound may be supported in the content of Table 1.

After sufficiently dispersing the pretreated silica support, the metallocene solution was introduced in the reactor, and the metallocene compound and methylaluminoxane were supported on the pretreated silica support while stirring for 30 minutes.

And then, stirring was stopped, and the temperature was lowered again to 30° C., followed by washing with a sufficient amount of toluene to remove unreacted aluminum compounds, and drying under vacuum to prepare a supported metallocene catalyst.

Example 2

A supported metallocene catalyst was prepared by the same method as Example 1, except using the pretreated silica support of Preparation Example 2 instead of the pretreated silica support of Preparation Example 1.

Example 3

A supported metallocene catalyst was prepared by the same method as Example 1, except using the pretreated silica support of Preparation Example 3 instead of the pretreated silica support of Preparation Example 1.

Comparative Example 1

A supported metallocene catalyst was prepared by the same method as Example 1, except using the silica support of Comparative Preparation Example 1 that was only dried at 600° C. for 12 hours instead of the pretreated silica support of Example 1.

Experimental Example

Ethylene polymerization was conducted under the conditions of Table 1, using the supported metallocene catalysts prepared in Examples 1 to 3 and Comparative Example 1.

Thereafter, the physical properties of each obtained polymer including the activity and the weight average molecular weight and the like were measured by common methods, and the results are summarized in the following Table 1.

The molecular weight and the molecular weight distribution were obtained by GPC (gel permeation chromatography) analysis using PI-GPC220 available from Agilent Technologies, Inc. The analysis temperature was 160° C., trichlorobenzene was used as a solvent, and the number average molecular weight (Mn) and the weight average molecular weight (Mw) were obtained by normalization to polystyrene. MWD was calculated by dividing the weight average molecular weight (Mw) by the number average molecular weight (Mn).

TABLE 1

|  | Example 1 | Example 2 | Example 3 | Comparative Example 1 |
|---|---|---|---|---|
| t-BuO(CH$_2$)$_6$MgCl treated amount (mmol/g-silica) | 0.5 | 1.0 | 1.5 | 0 |
| (nBuCp)$_2$ZrCl$_2$ supported amount (mmol/g-silica) | 0.05 | 0.05 | 0.05 | 0.05 |
| [MAO] (mmol/g-silica) | 8 | 8 | 8 | 8 |
| Polymerization temperature (° C.) | 90 | 90 | 90 | 90 |
| Polymerization pressure (Bar) | 40 | 40 | 40 | 40 |
| Activity (g/g-silica) | 5,700 | 6,400 | 6,150 | 5,300 |
| MWD | 3.7 | 5.4 | 4.3 | 2.8 |

Referring to the results of Table 1, it can be seen that Examples 1 to 3 of the present invention exhibit more excellent activities and broadened molecular weight distribution, compared to Comparative Example 1 wherein a metallocene catalyst using dried silica is used.

Specifically, since the silica support of the present invention has 3 kinds of reaction sites of —OH, —O-alkaline earth metal-halogen and —O-alkoxy (or —O-alkyl) on the surface, it may produce 3 kinds of active sites to MAO. Thus, according to the present invention, a metallocene catalyst having much broader molecular weight distribution compared to existing one may be prepared, even if the same metallocene catalyst is supported. Thereby, high quality polyolefin having desired properties may be prepared with excellent productivity using the metallocene catalyst.

The invention claimed is:

1. A silica support having reaction sites including —OH, —O—MgCl, —OR$_1$, —OR$_2$MgCl and —OR$_2$H, wherein R$_1$ is a C4-10 alkyl group and R$_2$ is a C6-10 alkylene group, on the silica surface.

2. The silica support according to claim 1, wherein the silica support has BET surface area of 200 to 800 m$^2$/g, and average particle diameter of 5 to 100 μm.

3. The silica support according to claim 1, further comprising oxide, carbonate, sulfate or nitrate of Na$_2$O, K$_2$CO$_3$, BaSO$_4$, or Mg(NO$_3$)$_2$.

4. A method for preparing a pretreated silica support according to claim 1, comprising
   (a) heat treating a silica-based support; and
   (b) pretreating the heat treated silica in (a) with 0.05 to 2 mmol/g-silica of an alkoxyalkyl-alkaline earth metal-halogen compound.

5. The method for preparing a pretreated silica support according to claim 4, wherein in the step (a), the silica-based support is heat treated at a temperature of 200 to 800° C. for 1 to 48 hours.

6. The method for preparing a pretreated silica support according to claim 4, wherein the silica-based support is silica, silica-alumina or silica-magnesia.

7. The method for preparing a pretreated silica support according to claim 4, wherein the silica-based support further comprises oxide, carbonate, sulfate or nitrate of Na$_2$O, K$_2$CO$_3$, BaSO$_4$, or Mg(NO$_3$)$_2$.

8. The method for preparing a pretreated silica support according to claim 4, wherein the step (b) further comprises progressing a reaction of the silica heat treated at 0 to 100° C. and an alkoxyalkyl-alkaline earth metal-halogen compound.

9. The method for preparing a pretreated silica support according to claim 4, wherein the alkoxyalkyl-alkaline earth metal-halogen compound is represented by the following Chemical Formula 3:

$$R_1OR_2MX \quad \text{[Chemical Formula 3]}$$

wherein, R$_1$ is a C1-10 alkyl group, R$_2$ is a C1-10 alkylene group, M is an alkaline earth metal, and X is a halogen atom.

* * * * *